United States Patent [19]
Wuthier et al.

[11] Patent Number: 5,932,611
[45] Date of Patent: Aug. 3, 1999

[54] ANGIOGENESIS INHIBITOR FOR THE TREATMENT OF CANCER

[75] Inventors: Roy E. Wuthier, Columbia, S.C.; Daotai Nie, Detroit, Mich.

[73] Assignee: University of South Carolina, Columbia, S.C.

[21] Appl. No.: 08/975,813

[22] Filed: Nov. 21, 1997

[51] Int. Cl.$^6$ ..................................................... A61K 31/35
[52] U.S. Cl. ............................................................ 514/456
[58] Field of Search .............................................. 514/456

[56] References Cited

PUBLICATIONS

W. Xie et al., "Isolation and structure identification of two new derivatives of the mycotoxin fusarochromenone produced by *Fusarium equiseti*," J Nat Prod 1995; 58:124–7.
J. C. Kim et al., "Sambutoxin, a new mycotoxin produced by toxic Fusarium isolates obtained from rotted potato tubers," Appl Environ Microbiol 1994; 60:4380–6.
M. W. Orth et al., "Avian tibial dyschondroplasia: a morphological and biochemical review of the growth plate lesion and its causes," Vet Pathol 1994;31:403–414.
M. E. Cook et al., "Factors influencing growth plate cartilage turnover," Poult Sci 1994; 73:889–96.
W. Wu et al., "Tibial dyschondroplasia of chickens induced by fusarochromanone, a mycotoxin," Avian Dis 1993; 37:302–9.
F. Minervini et al., "Immunomodulatory effects of fusarochromanones TDP–1 and TDP–2," Nat Toxins 1992; 1:15–18.
R. J. Pawlosky et al.,"Mass spectral analysis and fragment ion structure of fusarochromanone, "Biol Mass Spectrometry 1991; 20:743–9.
J. Yu et al., "Immunochromatography of fusarochromanone mycotoxins," J Assoc Off Anal Chem 1991; 74:655–60.
W. Wu et al., "Fusarochromanone production by Fusarim isolates," Appl Environ Microbiol 1990; 56:2989–93.
C. J. Mirocha et al., "Absence of trichothecenes in toxigenic isolates of *Fusarium moniliforme*," Appl Environ Microbiol 1990; 56:520–5.
J. S. Haynes et al., "Ultrastructure of Fusarium–induced tibial dyschondroplasia in chickens: a sequential study," Vet Pathol 1986; 23:499–505.
H. K. Abbas et al., "Mycotoxins produced by toxic Fusarium isolates obtained from agricultural and nonagricultural areas (Arctic) of Norway," Mycopathologia 1989; 105:143–51.
P. Krogh et al., "Natural occurrence of the mycotoxin fusarochromanone, a metabolite of *Fusarium equiseti*, in cereal feed associated with tibial dyschondroplasia," Appl Environ Microbiol 1989; 55:3184–8.

H. K. Abbas et al., "Production of trichothecene and non-–trichotecence mycotoxins by Fusarium species isolated from maize in Minnesota," Mycopathologia 1989; 108:55–8.
W. Xie et al., "Biosynthesis of fusarochromanone and its monoacetyl derivative by *Fusarium equiseti*," Appl Environ Microbiol 1989; 55:794–7.
C. J. Mirocha et al., "Mycotoxin production by *Fusarium oxysporum* and *Fusarium sporotrichioides* isolated from Baccharis spp. from Brazil," Appl Environ Microbiol 1989; 55:254–5.
E. M. Lawler et al., "Acid phosphatase activity of chondroclasts from Fusarium–induced tibial dyschondroplastic cartilage," Avian Dis 1988; 32:240–5.
M. M. Walser et al., "Effect of dietary selenium on the development of Fusarium–induced tibial dyschondroplasia in broiler chickens," Avian Dis 1988; 32:84–8.
G. C. Wright, Jr. et al., "Effect of fusarochromanone and T–2 toxin on articular chondrocytes in monolayer culture," Fundam Appl Toxicol 1987; 9:595–7.
J. Yu et al.,"Production and characterization of antibody against fusarochromanone," Food & Agricult Immun 1990; 2:55–64.
Daotai Nie et al., "Defect in Formation of Functional Matrix Vesicles by Growth Plate Chondrocytes in Avian Tibial Dyschondroplasia: Evidence of Defective Tissue Vascularization," Journal of Bone and Mineral Research 1995; 10:1625–1634.
Sadanand V. Pathre et al., "The structure of fusarochromanone: new mycotoxin from *Fusarium roseum*, "Graminearum"," Can. J. Chem. 1986; 64:1308–1311.
Shannon Brownlee, "They called his theory ridiculous," U.S. New & World Report 1996, p. 82.
Yin–won Lee et al., "TDP–1, a Toxic Component Causing Tibial Dyschondroplasia in Broiler Chickens, and Trichothecenes from *Fusarium roseum* 'Graminearum'," Applied and Environmental Microbiology 1985; pp. 102–106.
Pathre et al., Can. J. Chem., 64(7), 1308–11 Abatract Only, 1986.

*Primary Examiner*—Jerome D. Goldberg
*Attorney, Agent, or Firm*—Dority & Manning, P.A.

[57] ABSTRACT

The present invention provides a treatment for angiogenic diseases, including solid tumors. The treatment consists of administering therapeutically active dosages of FC101, resulting in a reduction in endothelial cell proliferation and inhibition of new blood vessel formation. FC101 can also be used as a lead compound to develop other pharmacologically-active compounds, by adding or substituting different functional groups for those already present on the FC101 molecule.

11 Claims, 8 Drawing Sheets

ANGIOGENESIS INHIBITOR FOR THE TREATMENT OF CANCER

FIELD OF THE INVENTION

The present invention is directed to the field of treating angiogenic diseases. Specifically, the invention relates to the use of FC101 as a chemotherapeutic agent for the treatment of cancer and other angiogenic diseases, and as a lead compound for developing other such pharmacologically-active agents.

BACKGROUND OF THE INVENTION

Angiogenesis is the development of new blood vessels from existing capillaries. This process has been implicated in a number of human diseases, as well as in the growth and metastasis of solid tumors. In some forms of arthritis, new capillaries form in the joint, leading to its gradual destruction. Solid tumors also must stimulate the formation of new blood vessels in order to obtain the nutrients and oxygen necessary for their growth, thus providing a route by which the tumors can metastasize to distant sites.

Experimental evidence has suggested that malignant tumors can induce angiogenesis through the elaboration of a variety of factors, such as acidic fibroblast growth factor (aFGF), basic fibroblast growth factor (bFGF), vascular endothelial growth factor (VEGF), platelet derived growth factor (PDGF), transforming growth factor-$\alpha$ (TNF-$\alpha$), and many others (Liotta et al., 1991, *Cell* 64: 327–336; Hanahan et al., *Cell* 86: 353–364).

A number of compounds have been discovered or developed which inhibit one or more of the factors or steps involved in angiogenesis. Several of these inhibitors are currently undergoing clinical evaluation in cancer trials. For example, Platelet Factor 4 is a 28 kDa tetrameric protein, which down-regulates aFGF receptors and inhibits endothelial cell proliferation and capillary tube formation. It also inhibits tumor-induced angiogenesis in vivo. The polysaccharide DS4152 inhibits bFGF binding to endothelial cells and cell proliferation, and has been shown to inhibit tumor angiogenesis and growth. FR111142, currently in Phase II cancer trials, is preferentially cytostatic to endothelial cells and inhibits collagenase activity. The identification of additional biologically active agents to inhibit angiogenesis would be highly desirable, because of their potential in providing effective treatment for cancer, arthritis, and other angiogenic diseases.

Members of the Fusarium species are distributed worldwide as soil inhabitants and parasites of cultivated plants. Some isolates of the species are capable of producing mycotoxins, the ingestion of which has been associated with a variety of animal intoxications. For example, chicks fed diets containing a 5% level of crude fungus cultures from *Fusarium equiseti* develop a syndrome known as Avian Tibial Dyschondroplasia (ATD), characterized by bone deformation and failure of cartilage calcification (Walser et al., 1982, *Vet Pathol* 19: 544–550).

A water soluble component from Fusarium cultures, fusarochromanone (FC), has been purified and characterized (Pathre et al., 1986, *Can. J. Chem* 64: 308–311), and one form of this compound, designated FC101 and having the chemical formula: 5-amino-2,2-dimethyl-6-[3'-(R, S) amino-4'-hydroxy-butan-1-one]-2,3-dihydro-4H-1-benzopyran-4-one, has been shown to cause ATD when administered to day-old broiler chicks (Lee et al., 1985, *Appl Environ Microbiol* 50:102–107).

Various hypotheses have been promulgated to explain the mechanism by which FC101 causes ATD. These include a direct effect on the matrix vesicles, the cell-derived structures which initiate the mineral formation necessary for growth plate calcification, or an inhibitory effect on the ability of growth plate chondrocytes to deposit mineral.

The vascular invasion of growth plate cartilage, also known as neovascularization or angiogenesis, is a process of new capillary formation from pre-existing vessels. The process involves several steps, including the degradation of the extracellular matrix around a local venule; migration of the endothelial cells (EC) lining the inner wall of blood vessels; proliferation of the EC; the resulting formation of capillary tubes; and, finally, the survival and maturation of newly formed blood vessels (Benjamin and Keshet, 1997, *Proc. Natl. Acad. Sci. USA* 94:8761–8766; Brooks et al., 1994, *Cell* 79:1157–1164). The present inventors hypothesized that the underlying pathogenicity of ATD results from a defect in the vascularization in affected areas of growth plate cartilage, although the reasons for this defective vascularization were unknown (Nie et al., 1995, *J Bone Miner Res* 10: 1625–1634).

The present invention relates to the discovery that a water soluble compound extracted from fungal cultures demonstrates a selective toxicity towards endothelial cells. This selective toxicity inhibits angiogenesis, and thus prevents capillary formation from pre-existing blood vessels.

In addition to fusarochromanone production, some members of the Fusarium genus have previously been shown to produce a number of biologically active compounds; some useful as pharmaceutical agents. Sawada et al., in U.S. Pat. No. 4,579,819, described a method for the production of ursodeoxycholic acid, useful in the therapy of cholesterol gallstones, by using microbial transformation with members of the Fusarium genus. Burmeister, in U.S. Pat. No. 3,959,468, disclosed an antibiotic produced by *Fusarium equiseti*, which was shown to have biological activity against several genera of gram negative bacteria.

Biological agents have also been extracted from the mycelium of a Fusarium. Specifically, Simon-Lavoine et al, in U.S. Pat. No. 4,233,291, disclosed a depsipeptide extracted from *Fusarium equiseti*, which stimulated the body's defenses when administered in pharmaceutical compositions. The depsipeptide was particularly useful in human and veterinary therapy for the treatment of chronic or acute respiratory diseases, such as chronic bronchitis and emphysema. Additionally, intraperitoneal administration of 50 μg of the depsipeptide was shown to increase the survival time of mice previously inoculated with 1000 L1210 leukemic cells and treated with cyclophosphamide.

Anti-leukemic activity and low toxicity in mice was also demonstrated for a novel antibiotic disclosed in Japanese Application No. 4036-276-A from Tayca Corporation. However, neither the molecular structure of this compound, nor that of the depsipeptide disclosed by Simon-Lavoine et al, is identical to that of FC101.

SUMMARY OF THE INVENTION

It is an object of the present invention to provide a treatment for angiogenic diseases in humans and animals.

Another object of the present invention is to provide a lead compound for use in the development of novel chemotherapeutic agents for the treatment of neoplasia and other angiogenic diseases.

A further object of the present invention is to provide a treatment to selectively inhibit endothelial cell proliferation.

A still further object of the present invention is to provide FC101 as a treatment for angiogenic diseases in humans and animals.

The present invention provides a treatment for angiogenic diseases in humans and animals. In particular, the present invention relates to the use of a water soluble fusarochromanone, FC101, extracted from *Fusarium equiseti* cultures, as an inhibitor of angiogenesis. FC101 exhibits selective toxicity towards vascular endothelial cells, resulting in reduced endothelial cell proliferation, and preventing tube/cord-like structure formation, which are essential steps in the formation of new blood vessels.

Further, applicants have found that the toxicity resulting from FC101 treatment is selective for endothelial cells, since treatment of growth plate chondrocytes has no significant inhibitory effect on the growth of established cell cultures, or on the ability of these cells to deposit minerals. Therefore, the selective effect of FC101 treatment on endothelial cells, which inhibits the essential steps required for the formation of new blood vessels, is useful as a treatment for diseases whose pathology requires angiogenesis.

Treatment with FC101 results in a breakdown of newly formed capillaries, an inhibition of DNA synthesis in endothelial cells, and a reduction in endothelial cell proliferation. Further, the formation of the tube/cord-like structures required for angiogenesis to proceed is prevented. The mode of action of FC101 is highly selective for endothelial cells, since treatment of established cultures of growth plate chondrocytes results in little or no significant inhibition of cell growth. This selective effect of FC101 towards endothelial cells, and the resulting inhibition of angiogenesis, supports its use as a therapeutic treatment for solid tumors and other angiogenic diseases.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, wherein.

DETAILED DESCRIPTION OF PREFERRED EMBODIMENT

Figure 1:
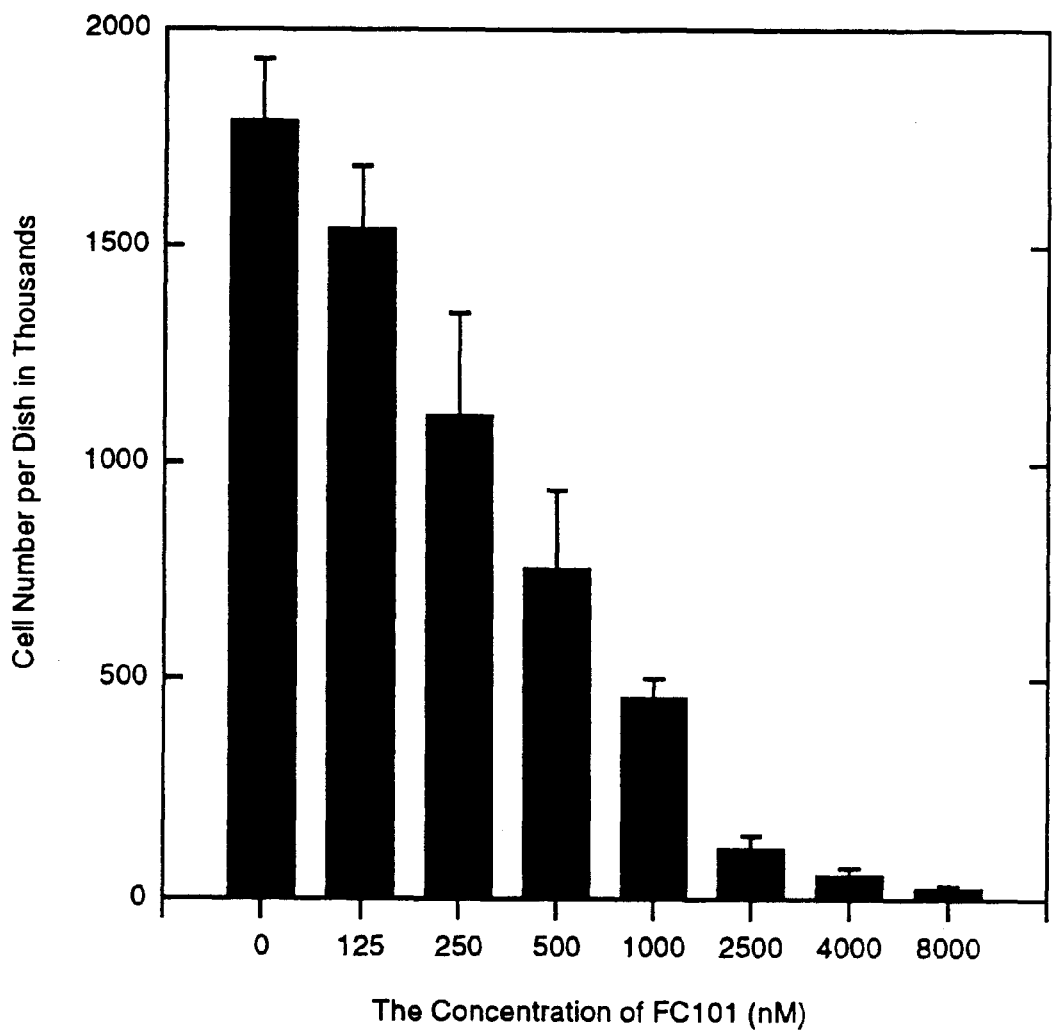
FIG. 1 is a graph that demonstrates dose-dependent reduction of endothelial cell numbers following FC101 treatment.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction.

The inhibition of angiogenesis in humans or in animals can be achieved by the present method of treatment, comprising the administration of a therapeutically active dosage of a water soluble compound isolated and purified from Fusarium fungal cultures. Specifically, the preferred mode employs administering FC101, derived from *Fusarium equiseti* cultures, as a treatment to selectively reduce endothelial cell proliferation, prevent the formation of the tube/cord-like structures required for the formation of new blood vessels, and break down newly formed capillaries, thus inhibiting angiogenesis. The mode of action of FC101 is highly selective for endothelial cells, since treatment of established cultures of growth plate chondrocytes results in little or no significant inhibition of cell growth.

FC101 can be used as a chemotherapeutic agent for the treatment of cancer and other angiogenic diseases. One such use for FC101 is as a treatment for cancerous tumors, by inhibiting the formation of new blood vessels required to supply nutrients and oxygen necessary for tumor growth and metastasis.

Treatment with FC101 can be administered in dosages and by techniques well known to those skilled in the medical or veterinary arts, taking into consideration such factors as the age, sex, weight, species and condition of the particular patient, and the route of administration. The route of administration can be percutaneous, via mucosal administration (e.g., oral, nasal, anal, vaginal) or via a parenteral route (intradermal, intramuscular, subcutaneous, intravenous, or intraperitoneal). FC101 can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. FC101 may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "REMINGTON'S PHARMACEUTICAL SCIENCE," 17th edition, 1985 may be consulted to prepare suitable preparations, without undue experimentation.

As mentioned above, the effective dosage and route of administration are determined by the therapeutic range and nature of the compound, and by known factors, such as the age, weight, and condition of the host, as well as $LD_{50}$ and other screening procedures which are known and do not require undue experimentation. Dosages can generally range from a few hundred milligrams to a few grams.

The chemical structure of FC101 (5-amino-2,2-dimethyl-6-[3'-(R,S) amino-4'-hydroxy-butan-1-one]-2,3-dihydro-4H-1-benzopyran-4-one)has previously been determined. The general structure, as described by Pathre et al., 1986, *Can J Chem* 64: 308–311), is as follows:

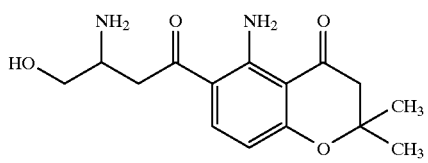

In accordance with standard methods well known to those skilled in the art, FC101 can be used as a lead compound to create analog compounds. Analog compounds possess similar biological functions, but differ in their chemical structure. Such compounds may be created by substituting different functional groups, such as methyl, acetyl, amino or hydroxyl groups, for those already present on the parent compound. Additional functional groups may also be added to the parent FC101. The resulting compounds may exhibit more desirable therapeutic properties, or be more pharmacologically active, than the parent molecule, FC101. Standard texts, such as "PRINCIPLES OF MEDICINAL CHEMISTRY," William O. Foye, Thomas L. Lemke, and David A. Williams, editors, 4th ed., 1995, may be consulted to produce such compounds, without undue experimentation.

The following examples are meant to be exemplary procedures only which aid in the understanding of the present invention. The invention is not meant to be limited thereto.

EXAMPLE 1

Preparation of FC 101

One method of producing FC101 is by purifying crude *Fusarium equiseti* fungal cultures, although the invention is not limited to the employment of *F. equiseti* inocula, but clearly also includes using other members of the Fusarium genera which produce water soluble fusarochromanones.

Cultures were established by seeding potato dextrose agar (PDA) plates, or other media suitable to support fungal growth, with soil particles containing *Fusarium equiseti*. Seeded PDA plates were incubated for five days at room temperature, then agar plugs containing the *Fusarium mycelium* were taken from the growing edge of the colonies and used as inocula. In one liter Erlenmeyer flasks, approximately 200 g of parboiled white rice and 120 ml of distilled water was autoclaved under standard conditions for 1 hour, twice on two consecutive days. The rice was inoculated with the mycelium plugs from 5-day-old cultures and maintained at room temperature. During the first week, the flasks were hand-shaken daily to provide uniform growth of the mycelium. After four weeks, the rice cultures were harvested, dried, and stored in the freezer until further use.

EXAMPLE 2

Purification of FC 101

One method of purifying FC101 from dried fungal cultures is a modification of the method used by Lee et al (1985, *Appl Environ Microbiol* 50: 102–107), as follows. Dried crude rice cultures (250 g), prepared as in Example 1, were extracted with chloroform-methanol-ammonium hydroxide (90:10:1, 1 liter each for five times). The extracts were vacuum filtered, pooled, and concentrated in vacuo to dryness, and dissolved in 100 ml of distilled water. The water phase was applied directly to a column packed with Amberlite XAD-2 (75 g, 20–50 mesh), washed and activated by extraction with acetone overnight and rinsed with distilled water before use. After sample application, the column was rinsed with 500 ml of distilled water and eluted with 500 ml of 90% methanol. The methanol elute was concentrated in vacuo and reconstituted to a final volume of 25 ml anhydrous methanol. The reconstitute was then applied onto a column packed with 60 g of silica gel 60 (70–230 mesh). Successive elutions were carried out with 500 ml of chloroform-methanol (9:1), followed by 500 ml of chloroform-methanol-ammonium hydroxide (90:10:1), with 50 ml of eluate being collected for each fraction. FC101 was eluted with the chloroform-methanol-ammonium hydroxide step. The FC fraction was monitored by viewing the column with long wavelength (360 nm) UV light. To verify the presence of fusarochromanone, 8 μl samples from each fraction were applied to the origin of 10×10 cm, 200 mm thick, Whatman LHP-K linear-K HPTL silica gel plates and developed with chloroform-methanol (80:20). The plate was then air-dried and the presence of fusarochromanone detected with UV light. Its presence was further demonstrated by use of a charring reagent (10% $CuSO_4$ in 8% $H_3PO_4$).

FC-containing fractions were pooled, dried in vacuo, dissolved in 25 ml of methylene chloride, and evaporated under nitrogen gas to yield a precipitate of FC. The amount of FC101 was determined by measuring the absorption at 383 nm using an extinction coefficient of 11,700 (Pathre et al., 1986, *Can J Chem* 64: 308–31 1).

FC101, as prepared above, was used in the following Examples, however, FC101 prepared from other Fusarium strains can also be used.

EXAMPLE 3

FC101 Treatment Inhibits Endothelial Cell Proliferation

Endothelial cell proliferation is required for angiogenesis. When preconfluent endothelial cell cultures were treated with graded nanomolar (nM) levels of FC101, progressive inhibition of cell proliferation was observed.

Endothelial Cell Culture Technique: Bovine aortic endothelial cells (EC) were cultured in suitable commercial media, such as Dulbecco's modified Eagle's medium (DMEM), supplemented with 15% fetal bovine serum (FBS). The cells were passaged by the EDTA-trypsin procedure. To test the effect of FC101 on endothelial cell proliferation, the cells were plated in 35 mm Petrie dishes at a density of 20,000 cells/$cm^2$ in DMEM with 15% FBS. Two days after plating, the preconfluent cells were treated with different concentrations of FC101 for two days. Each treatment involved four dishes. After treatment, the cells were then grown in normal DMEM with 15% FBS until the control cells reached full confluence. The cells were then trypsinized and counted with four repetitions. FIG. 1 shows the average cell numbers, along with standard deviation, from each of four dishes treated with various dosages of FC101. Results showed that FC101 treatment caused a dose dependent reduction in the numbers of endothelial cells. The FC101 concentration required for half inhibition of cell number was approximately 400 nM. At a concentration higher than 2.5 $\mu$M, the number of viable cells after FC101 treatment was less than the starting cell number, 0.2 million per dish.

EXAMPLE 4

FC101 Treatment Inhibits Cell Division in Endothelial Cells

Figure 2:
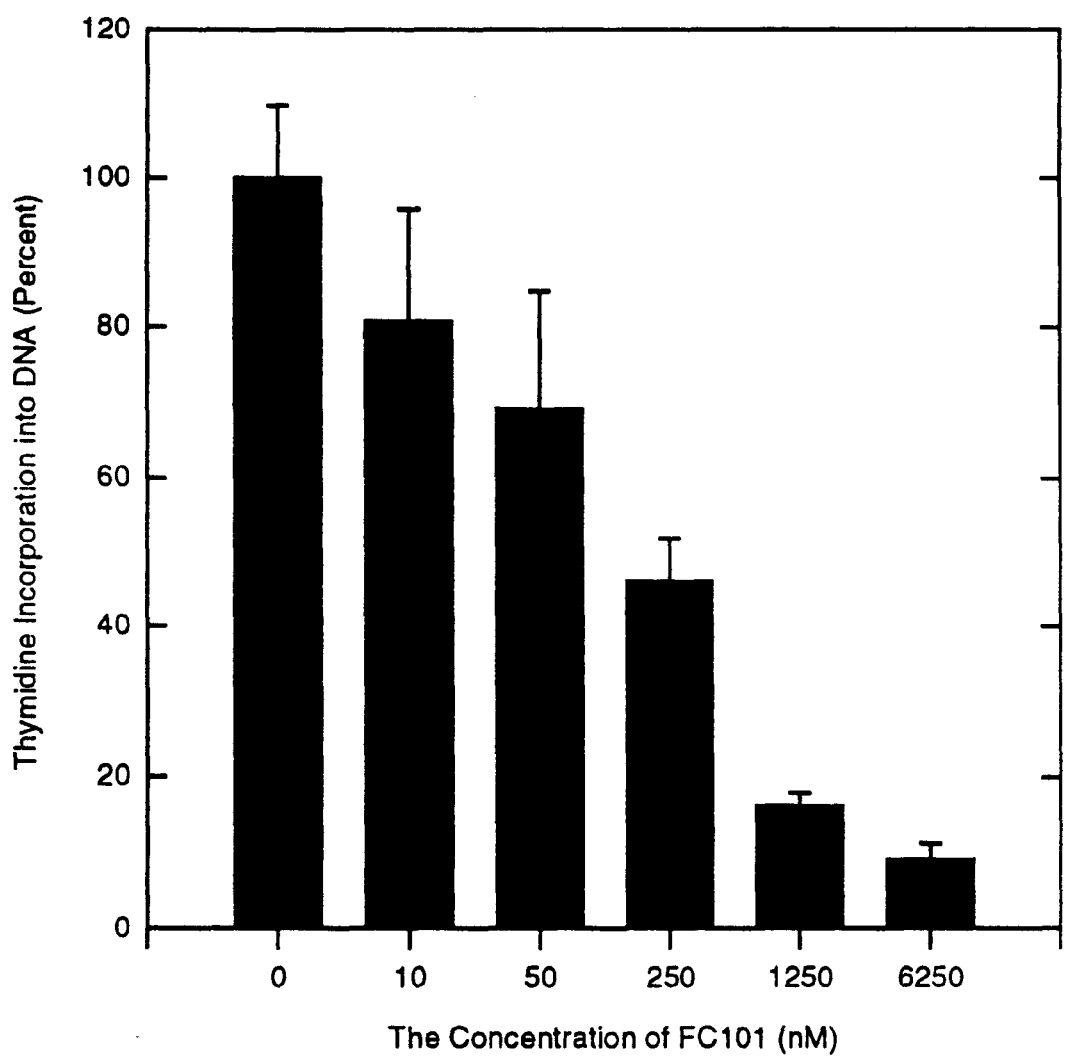
FIG. 2 is a graph that shows an inhibition of thymidine incorporation into DNA following treatment with varying amounts of FC101.

Two days after plating bovine aortic endothelial cells as described in Example 3, the cells were treated with different amounts of FC101 in fresh medium containing 1 $\mu$Ci/ml $^3$H-thymidine. Each treatment had four dishes. The treatment and labeling were continued for 24 hours. Then, the media was removed and the dishes washed twice with 1 ml cold TMS (N-tris methyl-2-aminoethane sulfonic acid-$Mg^{2+}$-sucrose buffer), twice with 2 ml of 10% trichloroacetic acid (TCA), and then rinsed with 1 ml of 95% ethanol/ether (3/1, v/v). After air drying, the cells were treated with 0.5 ml of 0.2 M NaOH for 15 minutes and then neutralized with 0.5 ml of 0.25 M acetic acid. An aliquot of 0.5 ml was mixed with 5 ml of scintillation fluid and counted in a beta-counter. FIG. 2 shows that FC101 treatment of endothelial cells reduces thymidine incorporation into DNA. The concentration of FC101 for half-inhibition of thymidine incorporation was approximately 150 nM.

EXAMPLE 5

FC101 Treatment Inhibits Spontaneous Tube/Cord Formation

Figure 3A:
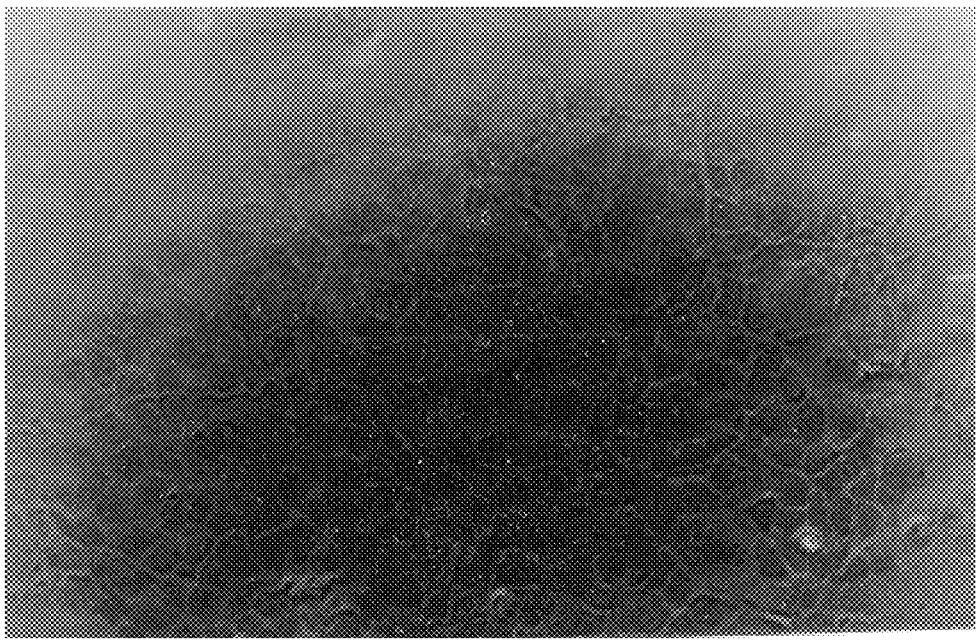
FIG. 3A is a photograph that shows the spontaneous formation of cord/tube-like structures in confluent cultures of Bovine endothelial cells.
Figure 3B:
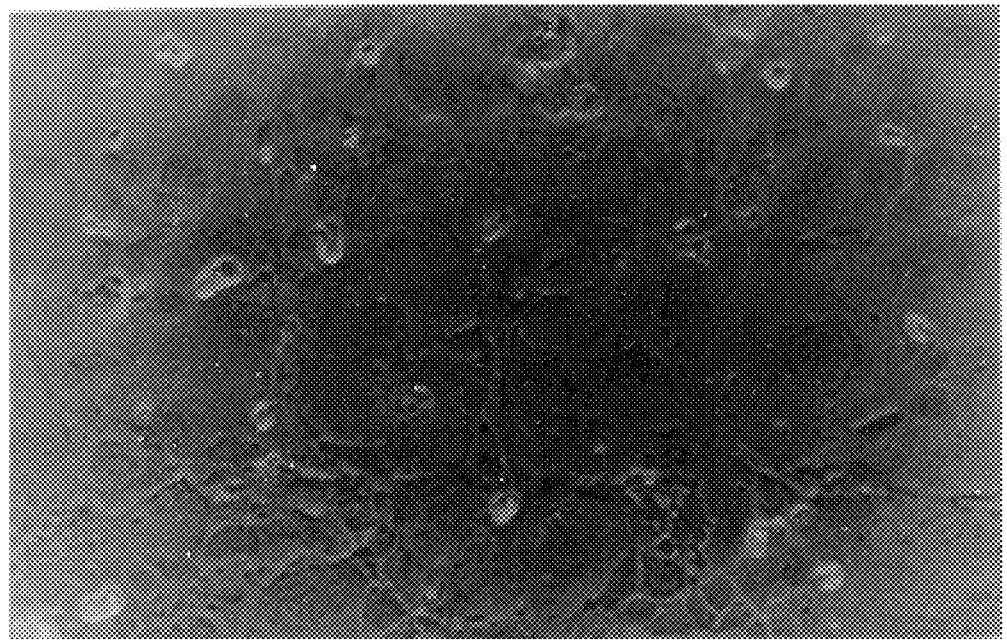
FIG. 3B is a photograph that demonstrates the inhibition of cord/tube-like structure formation in similar cultures treated for ten days with 0.5 µM FC101.

Confluent endothelial cell cultures, when maintained in Dulbecco's modified Eagle's medium (DMEM), supplemented with 10% fetal bovine serum (FBS) for a period of several weeks, can display various tube/cord-like structures (Folkman and Haudenschild, 1980, *Nature*, 288:551–556). The formation of these structures is an essential step in angiogenesis. Bovine endothelial cells were plated at a density of 20,000 cells/cm$^2$ as described in Example 3. To increase the spontaneous tube/cord formation, the culture medium was supplemented with 10 ng/ml of basic fibroblast growth factor (bFGF) and 1 ng/ml of transforming growth factor (TGF-$\beta$). Two days after plating, the cells were treated with 0.5 $\mu$M FC101 continuously for ten days. As seen in FIG. 3, control cultures 3A demonstrated the formation of cord/tube-like structures, while FC101-treated cells 3B did not. Pictures shown were taken on Day 10 after plating.

EXAMPLE 6

FC101 Treatment Results in a Breakdown of Newly Formed Capillaries

Figure 4A:
FIG. 4A is a photograph showing the normal appearance of chicken chorioallantoic membrane surrounding a 0.5% methylcellulose control disk.
Figure 4B:
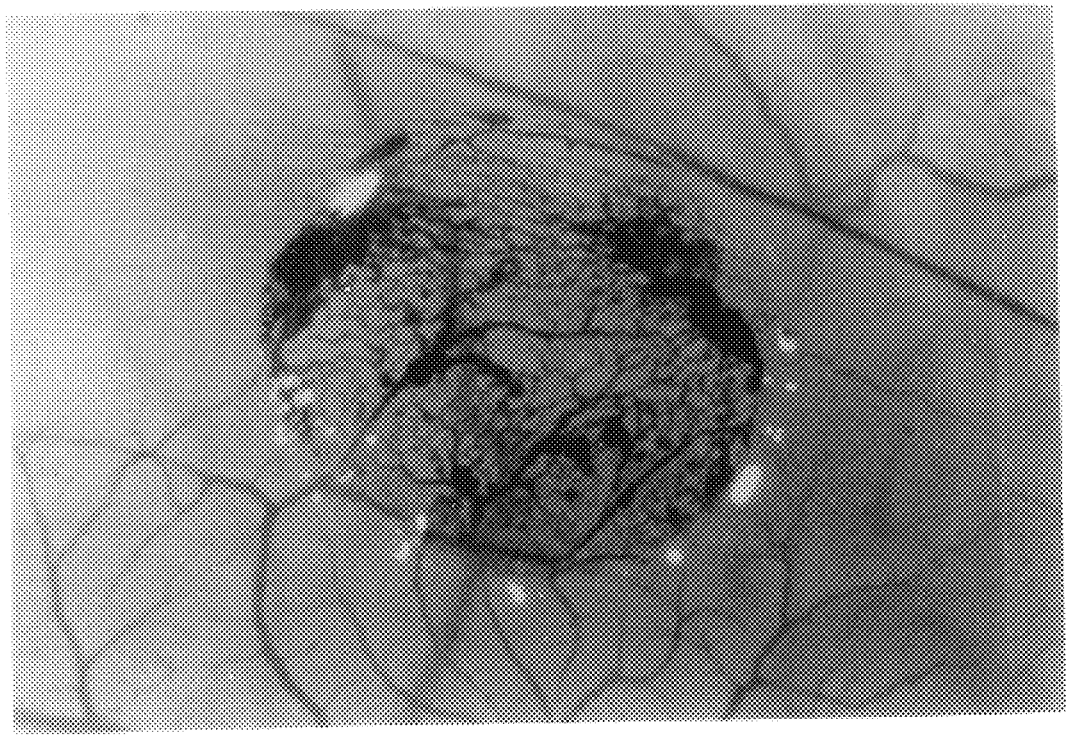
FIG. 4B is a photograph that demonstrates microhemorrhage in the chorioallantoic capillaries around the disc containing 10 µg of FC101.
Figure 5A:
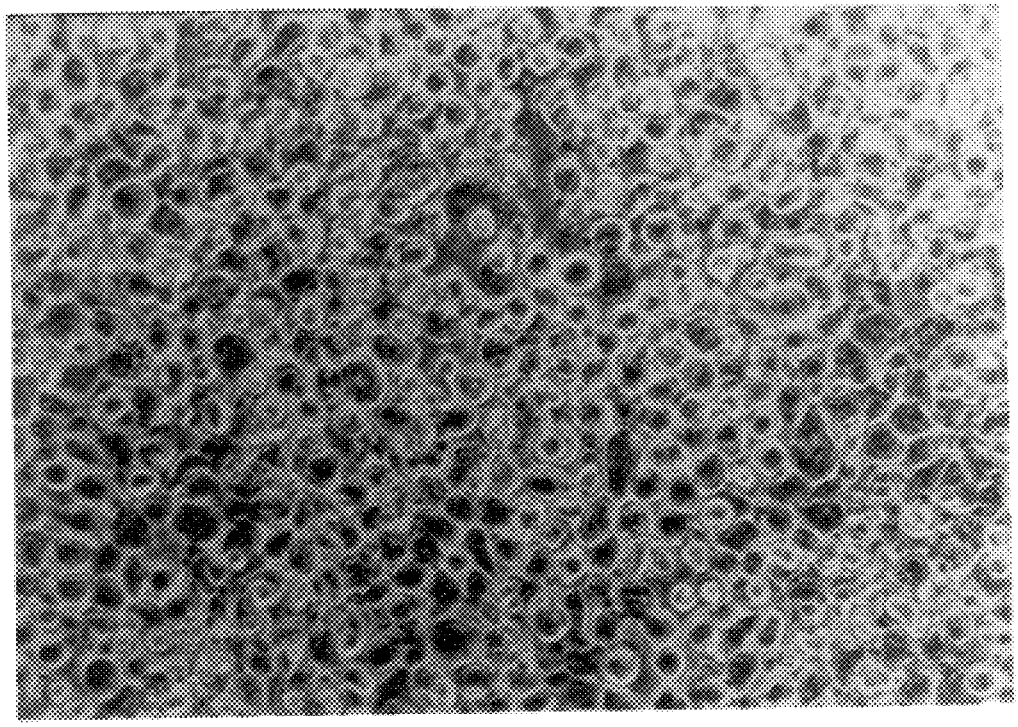
FIG. 5A is a photograph demonstrating the morphology of cultured growth plate chondrocytes, obtained from the tibiae of 6–8 week old broiler chickens.
Figure 5B:
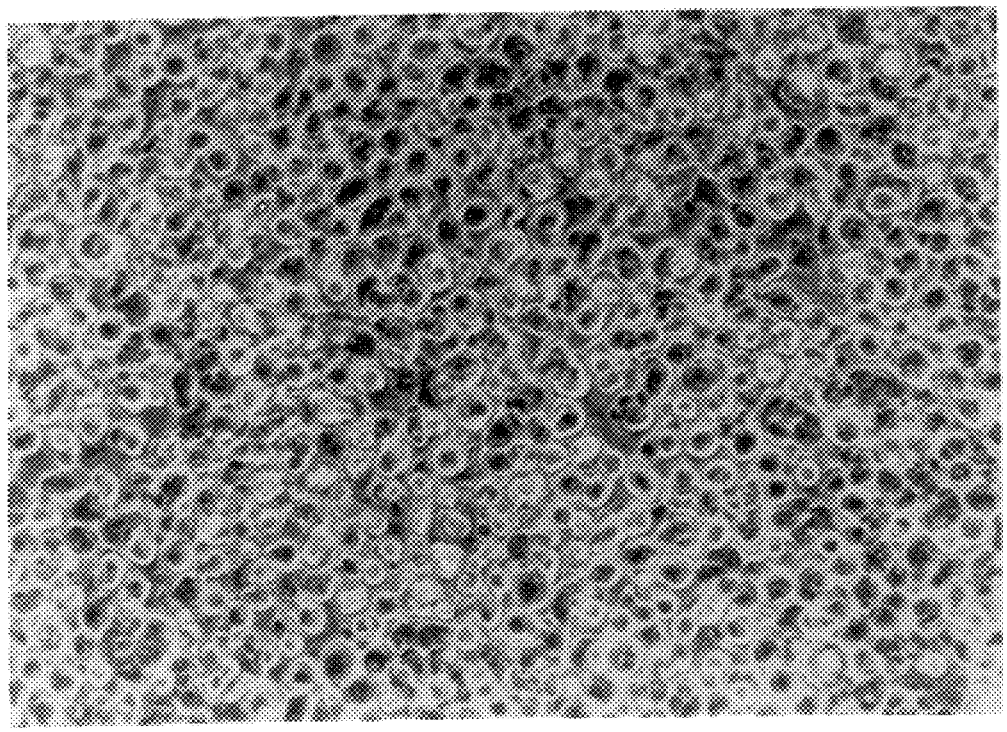
FIGS. 5B, 5C, and 5D are photographs of the chondrocyte cultures treated with FC101 for seven days, at dosages of 0.6 µM; 3 µM; and 15 µM, respectively, showing that FC101 does not affect cell growth.
Figure 5C:
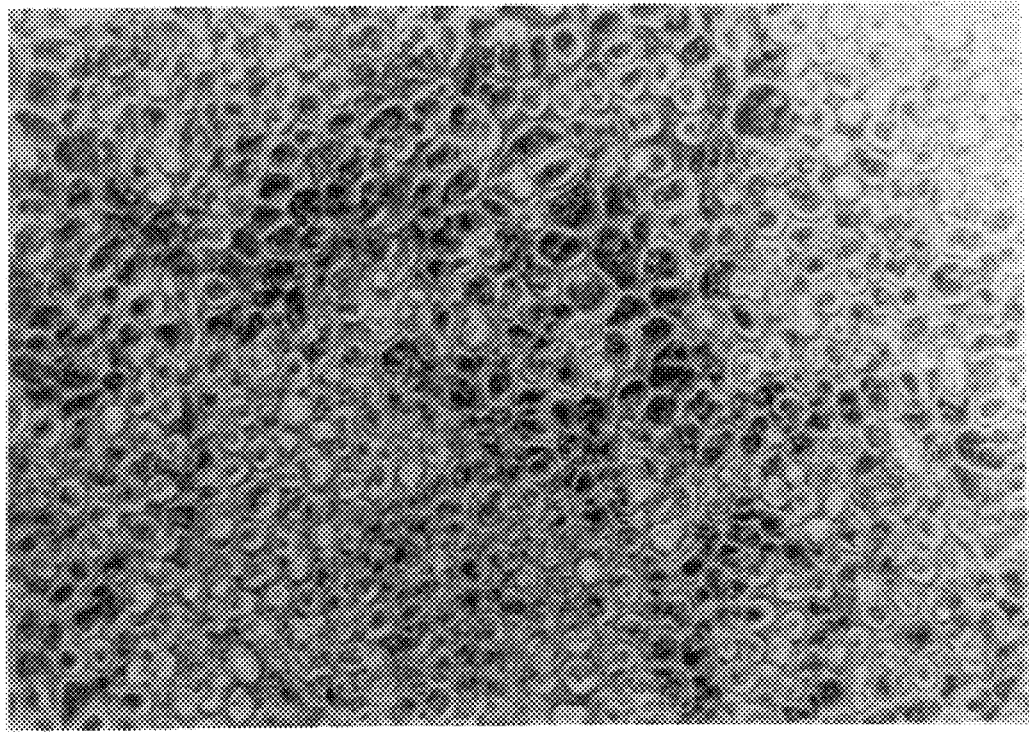
Figure 5D:
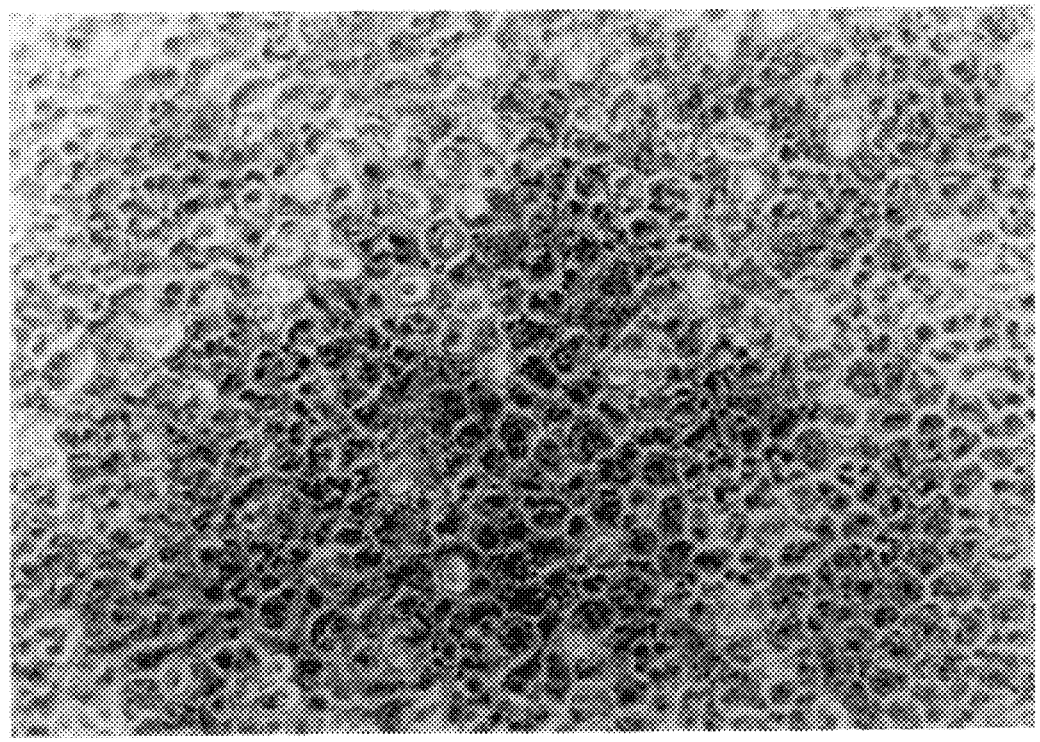

To determine the potential for FC101 treatment to induce microhemorrhage in newly formed capillaries, a chicken chorioallantoic membrane (CAM) assay was performed as a modification of the procedure of Moses et al., (1990, *Science* 248: 1408–1410). Fertile chicken eggs were incubated at 37° C. in a humidified chamber. After three days of incubation, the embryos were carefully removed from their shells and transferred to sterile 10 cm diameter Petrie dishes. Methylcellulose disks were prepared by adding specified amounts of FC101 to sterile 0.5% methylcellulose solutions to produce the desired final concentration. A small volume (10 $\mu$l) of this solution was pipetted onto a hydrophobic plastic plate and dried under a sterile hood, forming a small thin disk. From day 6 of development, methylcellulose disks containing a specified amount of FC101 were placed on the allantoic membrane. The effect of FC101 on the formation and integrity of capillary blood vessels was observed under a dissecting stereo-microscope. Methylcellulose disks containing 10 $\mu$g FC101 or more induced the breakdown of newly formed blood vessels in the chorioallantoic capillaries that underlie the disk within minutes of placement, while the control disks, containing methylcellulose alone, did not. Six-day old chick embryos are shown in the photographs in FIG. 4. Pictures shown were taken within 15 minutes after the application of the disks. Areas of blood vessel breakdown underlie the methylcellulose disk containing 10 $\mu$g FC101 (FIG. 4B), while intact vasculature can be observed in the membrane surrounding the control disk (FIG. 4A).

EXAMPLE 7

FC101 Treatment Does Not Affect Morphology of Cultured Chondrocytes

When growth plate chondrocytes, from day 7 or later cultures, were treated with 0.6 to 15 $\mu$M FC101, there were no appreciable morphological changes noted associated with either short or long term treatment.

Isolation and Culture of Growth Plate Chondrocytes: Six-to eight-week old broiler chickens were obtained commercially, sacrificed by cervical displacement, and the tibiae harvested. Epiphyseal growth plate chondrocytes were obtained from the tibiae as described (Ali et al., 1970, *Proc Natl Acad Sci USA* 67: 1513–1520). Briefly, cartilage slices were digested in 1 % trypsin solution prepared in synthetic cartilage lymph (SCL). SCL contains 2mM $Ca^{2+}$ and 1.42 mM Pi, in addition to 104.5 mM $Na^+$, 133.5 mM $Cl^-$, 63.5 mM sucrose, 16.5 mM N-tris methyl-2-aminoethane sulfonic acid (TES), 12.7 mM $K^+$, 5.55 mM D-glucose, 1.83 mM $HCO^{3-}$, 0.57 mM $Mg^{2+}$, and 0.57 mM $SO^{4-}$. Cartilage slices were digested for 15 to 20 minutes at 37° C. After digestion, part of the trypsin solution was removed and 10 ml of SCL and 0.5 ml of 0.78% collagenase solution added to the tissue slices. After 30 min of collagenase/trypsin digestion at 34° C., the liquid was removed from the slices and replaced with 0.5 ml of 0.78% collagenase solution plus 15 ml DMEM, with 10% FBS. The collagenase-DMEM solution was removed from the cartilage digestate after 15 hours (overnight) of digestion. The chondrocytes were released from the residual tissues by vortexing for a total of 3 min (1 min each time) in fresh medium. Isolated cells were demineralized in iso-osmotic citrate buffer (8.0 mM citric acid in 80.5 mM sodium citrate, pH 6.0) for 15 min at 34° C. After demineralization, cells were washed with fresh medium, resuspended in 10 ml of DMEM with 10% FBS, and counted using a hemocytometer. Cell viability was determined by trypan blue exclusion. Cells were plated at 3–4×10$^5$ cells per 35 mm dish in 2 ml of medium. The cells were initially cultured in DMEM with 10% FBS and 1 % penicillin/streptomycin solution. The culture medium was changed twice a week for the duration of the experiments. On day 7, the cell cultures were changed into a 1:1 (v/v) mixture of DMEM with 10% FBS and serum-free HL-1 medium. Ascorbic acid was provided at 50 $\mu$g/ml medium after day 3. For treatment of endothelial cell cultures, the concentrated fusarochromanone solution was diluted in methanol to final concentrations of 0.6, 3, 15 mM. On day 7, 2 $\mu$l samples of the FC solutions or pure methanol for the control were added to the cultures in 2 ml of media. FIGS. 5A to 5D show there is no appreciable change in the morphology of chondrocytes treated with FC101 for seven days. Note that there is little difference between the control cells (5A) and those treated with FC101 (B:0.6 μM; C:3 μM; D:15 μM FC101).

EXAMPLE 8

FC101 Treatment Does Not Affect Calcification Mediated by Collagenase-Released Matrix Vesicles Isolation of Collacqenase-Released Matrix Vesicles (CRMV):

Collagenase-released matrix vesicles (CRMV) were isolated from growth plate cartilage tissues, using the procedure of Wuthier et aL., (1978, *Metab Bone Dis Relat Res* 1: 125–136). Briefly, tissues were digested at 37° C. in 0.1% Trypsin in SCL for 20 min. This solution was removed, the slices rinsed with an equal volume of SCL, and digestion with collagenase (200 U/g tissue) at 37° C. continued for three hours. To harvest the matrix vesicles (MV), the partially digested tissue was vortexed and the suspension subjected to differential centrifugation at 13,000×g for 20 min to sediment the larger cell fragments, and at 10,000×g for 1 h to sediment the MV. The MV pellet was resuspended in $Ca^{2+}$-free SCL, or SCL containing one-half the normal level of $Ca^{2+}$. Protein concentration in the vesicles was determined according to the Lowry method. For each uptake tube, 50 μg of MV protein was incubated in 1 ml of SCL at 37° C. for varying time periods, and $Ca^{2+}$ uptake by vesicles determined by measuring the disappearance of $Ca^{2+}$ from the incubation medium. At timed intervals, 100 μl samples of the SCL were removed and centrifuged in Eppendorf tubes at 16,000×g for 10 min to separate the liquid and solid phases. Duplicate 25 μl samples of the supernatant fluid were used to determine the level of $Ca^{2+}$ remaining in the solution. The level of $Ca^{2+}$ was determined spectrophotometrically using the method of Baginsky et al. (1973, *Clin Chim Acta* 46: 46–54). Using the level of $Ca^{2+}$ in SCL as a reference, the percentage of $Ca^{2+}$ uptake was calculated as follows:

$$\text{Percentage of Ca}^{2+}\text{ Uptake} = \frac{[Ca^{2+}] \text{ at } T_0 - [Ca^{2+}] \text{ at } T_x}{[Ca^{2+}] \text{ at } T_0} \times 100$$

where $T_0$ is the initial time, and $T_x$ is the time at which the sample was removed.

Figure 6:
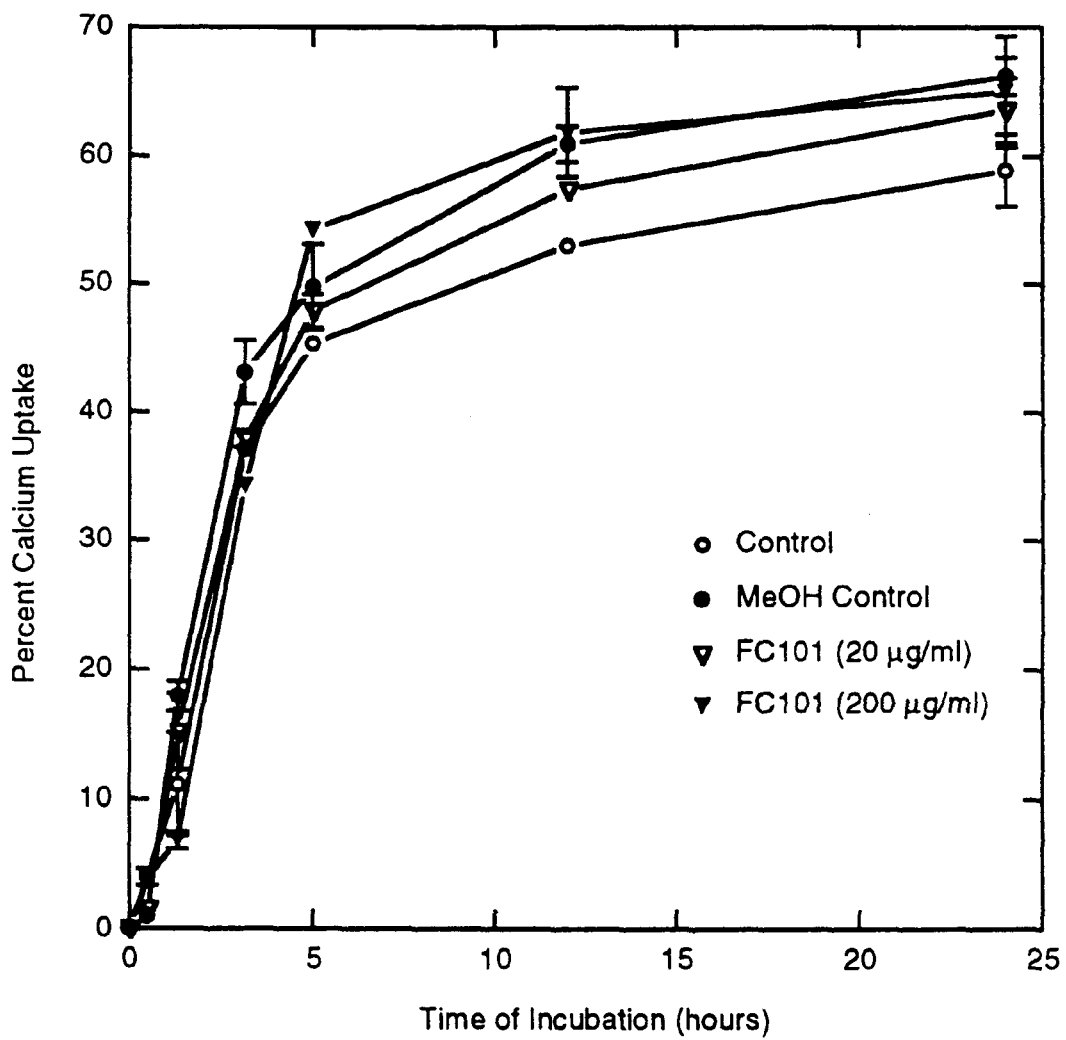
FIG. 6 is a graph depicting calcium uptake by collagenase-released matrix vesicles (CRMV), isolated from growth plate cartilage tissues, showing that FC101 does not inhibit calcification of these key structures.

For treatment, FC101, or vehicle methanol, was added to the SCL prior to the addition of CRMV during uptake studies. FIG. 6 shows the similar uptake kinetics among the different treatments, indicating that FC101 did not inhibit CRMV-mediated calcification, even at higher levels.

Figure 7:
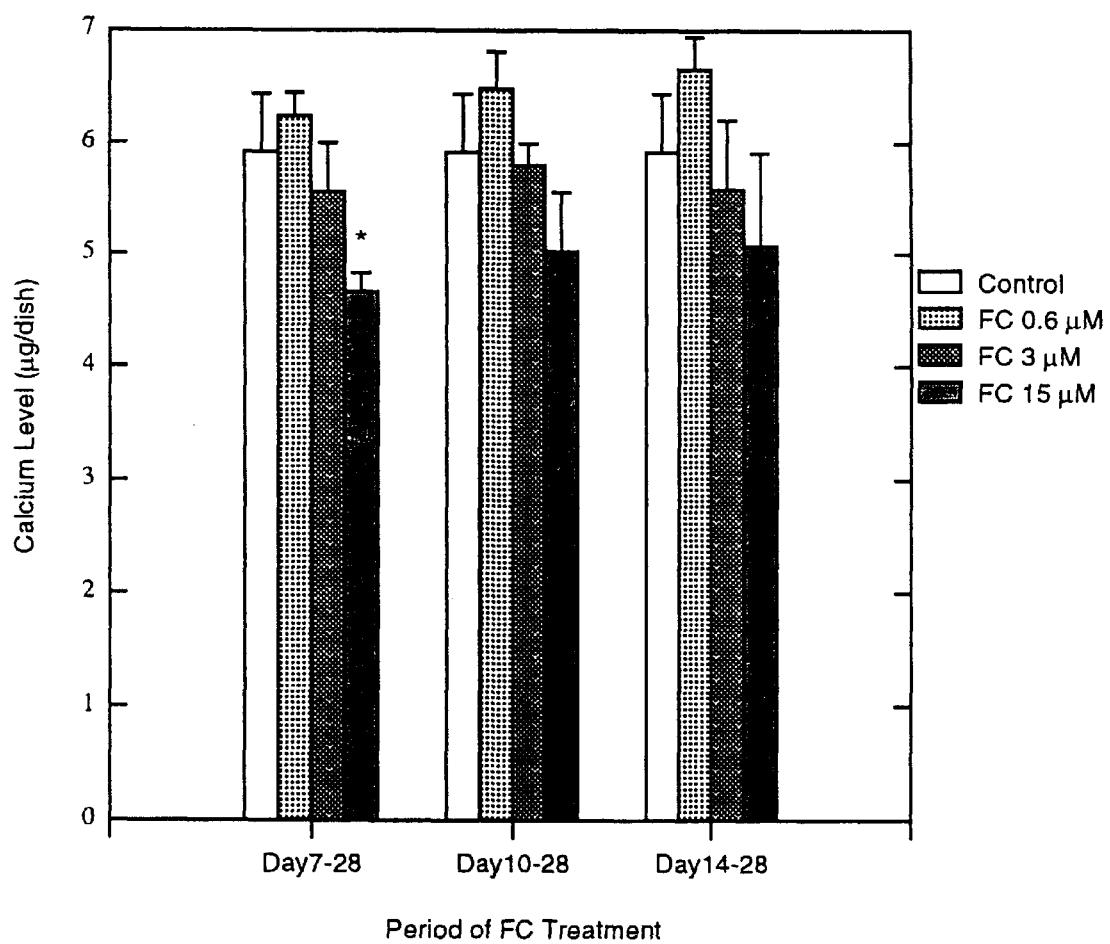
FIG. 7 is a graph that shows the effect of FC101 treatment on growth plate chondrocyte monolayers, at day 7, day 10, or day 14 of culture, showing that FC101 has only a minor or insignificant effect on overall calcium deposition by growth plate cells.

Continuous treatment of chondrocyte cultures with varying amounts of FC101 also does not significantly alter the mineralization pattern and morphology of chondrocytes, when treated from day 7 (preconfluent stage) until day 28. Graded levels of FC101 were added to the cultures starting at different stages: day 7 (preconfluent stage), Day 10, or Day 14 (confluent stage). The treatments were continued until Day 28, when the cultures were harvested. There were three culture dishes per treatment. FIG. 7 demonstrates a dose-dependant reduction of mineral deposition by higher levels (3 μM and 15 μM) of FC101, while a lower level (0.6 μM) of FC101 slightly stimulated mineral deposition. The reduction of mineral deposition in the cell monolayers resulting from treatment with the high dose of FC101 (15 μM) was not statistically significant when the treatments were started at later stages of culture (Day 10 or Day 14). However, when the treatment was started at Day 7, 15 μM FC101 did significantly (p<0.05) reduce mineral deposition.

Although a preferred embodiment of the present invention has been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole and in part.

What is claimed is:

1. A method for treating cancer sensitive to the compounds below in a patient, comprising administering to said patient a therapeutically active dosage of a composition comprising 5-amino-2,2-dimethyl-6-[3'-(R,S) amino-4'-hydroxy-butan-1-one]-2,3-dihydro-4H-1-benzopyran-4-one, wherein said composition is administered via a pharmaceutically or veterinarily acceptable carrier, for a time effective to treat said cancer by inhibiting the formation of new blood vessels in said patient.

2. A method according to claim 1, wherein said therapeutically active dosage is in the range of about 0.2 μg to about 200 g.

3. A method according to claim 1, wherein said composition is administered via a mucosal route.

4. A method according to claim 1, wherein said composition is administered via a parenteral route.

5. A method according to claim 1, wherein said cancer is a solid tumor sensitive to said compounds.

6. A method according to claim 1, wherein said pharmaceutically or veterinarily acceptable carrier is chosen from the group consisting of saline, glucose, sterile water and mixtures thereof.

7. A method for inhibiting metastasis sensitive to the compounds below in a patient comprising administering to said patient a therapeutically active dosage of a composition comprising 5-amino-2,2-dimethyl-6-[3'-(R,S) amino4'-hydroxy-butan-1-one]-2,3-dihydro-4H-1-benzopyran-4-one, wherein said composition is administered via a pharmaceutically or veterinarily acceptable carrier, for a time effective to inhibit said metastasis by inhibiting the formation of new blood vessels.

8. A method according to claim 7, wherein said therapeutically active dosage is in the range of about 0.2 μg to about 200 g.

9. A method according to claim 7, wherein said composition is administered via a mucosal route.

10. A method according to claim 7, wherein said composition is administered via a parenteral route.

11. A method according to claim 7, wherein said pharmaceutically or veterinarily acceptable carrier is chosen from the group consisting of saline, glucose, sterile water and mixtures thereof.

* * * * *